(12) United States Patent
Bogema

(10) Patent No.: US 6,248,598 B1
(45) Date of Patent: Jun. 19, 2001

(54) IMMUNOASSAY THAT PROVIDES FOR BOTH COLLECTION OF SALIVA AND ASSAY OF SALIVA FOR ONE OR MORE ANALYTES WITH VISUAL READOUT

(76) Inventor: Stuart C. Bogema, 13222 Wates Spring Pl., Clifton, VA (US) 20124

( * ) Notice: Subject to any disclaimer, the term of this patent is extended or adjusted under 35 U.S.C. 154(b) by 0 days.

(21) Appl. No.: 09/154,890

(22) Filed: Sep. 17, 1998

(51) Int. Cl.[7] .................................................. G01N 33/533
(52) U.S. Cl. ........................ 436/518; 422/56; 422/57; 422/58; 422/60; 422/61; 422/68.1; 422/99; 435/7.1; 435/7.93; 435/7.94; 435/287.7; 435/287.8; 435/287.9; 435/970; 436/528; 436/530; 436/541; 436/810; 436/514
(58) Field of Search .................................. 422/56–58, 60, 422/61, 68.1, 99; 435/7.1, 7.93, 7.94, 287.7, 287.8, 287.9, 970; 436/518, 528, 530, 541, 810, 514

(56) References Cited

U.S. PATENT DOCUMENTS

| | | |
|---|---|---|
| 4,703,017 | 10/1987 | Campbell et al. . |
| 4,833,073 | 5/1989 | McNally et al. . |
| 5,087,556 * | 2/1992 | Ertinghausen . |
| 5,334,502 | 8/1994 | Sangha . |
| 5,376,337 | 12/1994 | Seymour . |
| 5,494,831 * | 2/1996 | Kindler . |
| 5,501,985 | 3/1996 | Baugher et al. . |
| 5,556,789 | 9/1996 | Goerlach-Graw et al. . |
| 5,580,794 | 12/1996 | Allen . |
| 5,714,341 | 2/1998 | Thieme et al. . |

FOREIGN PATENT DOCUMENTS

88/08534 * 3/1988 (WO) .

* cited by examiner

Primary Examiner—Christopher L. Chin
(74) Attorney, Agent, or Firm—Robin L. Teskin

(57) ABSTRACT

A device that provides for both the collection of saliva and detection of at least one analyte therein, e.g., a drug, is provided. This device provides for rapid analysis of saliva samples, while also providing a convenient assay method that does not require the addition of extraneous reagents, or other materials. Thereby, this device can be used by non-laboratory personnel without risk of user introduced errors.

7 Claims, 1 Drawing Sheet

Figure 1:
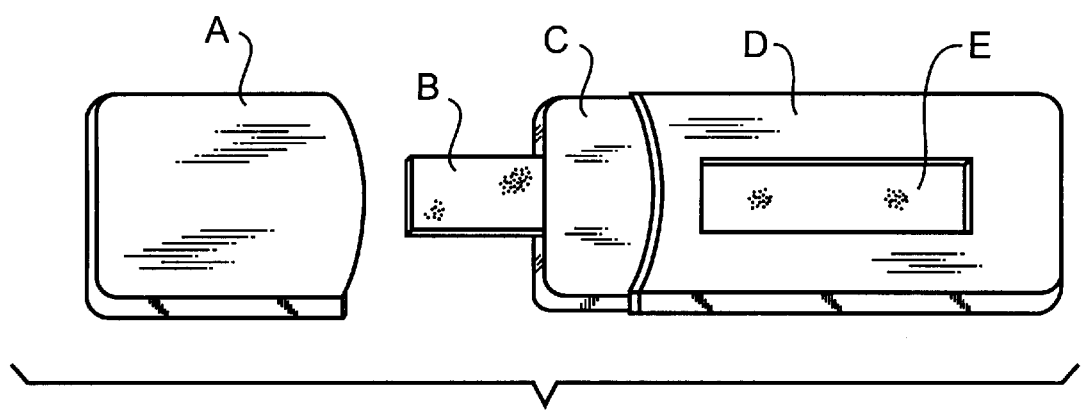

IMMUNOASSAY THAT PROVIDES FOR BOTH COLLECTION OF SALIVA AND ASSAY OF SALIVA FOR ONE OR MORE ANALYTES WITH VISUAL READOUT

FIELD OF THE INVENTION

The present invention relates to a device that directly collects saliva from the mouth and provides a solid phase assay of one or more analytes in the saliva and the use thereof as an assay device, e.g., for drug testing analysis.

BACKGROUND OF THE INVENTION

The determination of the presence and/or amount of analytes in biological fluids, such as blood and saliva, is a useful analytical method. For example, the detection of drugs of abuse in saliva can be useful for determining recent use of the drug by a person (W. Schramm et al, *Journal of Analytical Toxicology*, 16, 1–9, 1992, "Drugs of Abuse in Saliva: A Review").

Saliva has been used for therapeutic drug monitoring (I.A. Siegel et al, *Ann. NY Acad. Sci.*, 694, 86–90, 1993, "The Role of Saliva in Drug Monitoring"), the measurement of steroids and other endogenous compounds (J. M. Dabbs et al, *Clinical Chemistry*, 41, 1581–1584, 1995, "Reliability of Salivary Testosterone Measurements") and the measurement of nicotine metabolites (D. L. Colbert and M. R. Holmes, *Clinical Chemistry*, 40, 843–844, 1994, "Measurement of Salivary Cotinine with Abbott TDx"). Typically, saliva is collected separate from the analytical procedure. In general, the analysis of saliva for analytes is performed with instrumentation in a laboratory and is effected separate from the collection procedure and collection device.

A number of such saliva collection devices have been reported. (See, U.S. Pat. No. 5,334,502, U.S. Pat. No. 5,494,646, U.S. Pat. No. 5,393,496, and U.S. Pat. No. 5,376,337). However, none of these devices collects the saliva and initiates an assay or assays on the saliva simultaneously.

More specifically, U.S. Pat. No. 5,334,502 describes a method for collecting saliva and verifying the quantity of saliva collected. Similarly, U.S. Pat. No. 5,494,646 describes an apparatus for sampling saliva that consists of a sample collector and sample container. Also, U.S. Pat. No. 5,393,496 describes a saliva sampling device including a collection container, a saliva collector and a sample container. Still further, U.S. Pat. No. 5,376,337 describes a saliva sampling device that includes a sample container, a holding reservoir and a filter. Thus, all of such methods and devices provide for the collections of saliva only, and do not allow for both the simple collection of a saliva sample and the simultaneous analysis of analytes in the collected saliva without the need for manipulation of the sample or additional testing steps.

Many different types of assay methods for measuring an analyte in a sample, e.g., a biological fluid are known in the art. Many of such methods are immunological based, i.e., they involve measuring the binding of an antibody or antibody fragment to a complementary ligand, e.g., a drug or other molecule.

Immunoassay methods, in general, are based on the competition between a specific analyte, the concentration of which is to be measured in a sample, and a known amount of tracer, which is generally the analyte or an appropriate analog thereof in labeled form, with the analyte and tracer competing for a limited number of available binding sites on a binder which specifically binds the analyte and tracer. Immunoassays have been used in laboratories for over thirty years.

In some of such procedures, the binders are supported on a solid support such as a porous membrane, whereby the bound and free analytes and tracers of the assay in a liquid matrix, lateral flow by capillary action through the solid support and past the binder(s) and the competitive reaction takes place. In some of such procedures, the tracer is read visually. See e.g., U.S. Pat. No. 4,703,017 and U.S. Pat. No. 5,145,789.

Because of the desire and need for more convenient and less expensive diagnostic methods, there have been efforts in the last twenty years to develop simple tests to allow unskilled persons to perform certain analytical procedures outside of the laboratory. For example, U.S. Pat. No. 5,145,789 describes a device to test urine for human chronic gonadotropin as a means to detect pregnancy. The device is an immunoassay performed on a solid support membrane that provides a visual readout. However, unlike the present device, the specimen to be analyzed is urine rather than saliva and the collection of the urine is performed separate from the analysis.

Also, in the last twelve years there have been developed solid phase immunoassays with visual readouts such as U.S. Pat. No. 4,703,017. U.S. Pat. No. 5,556,789 describes a device for the simultaneous determination of several analytes by solid phase immunoassay with visual readout. U.S. Pat. No. 5,714,341 specifically describes a saliva assay method and device. However, the device requires separate collection of the saliva or other specimen prior to the addition of the specimen to the device. Thus, at least two operations and devices are necessary with these previous methods. First, collection of the saliva specimen with some type of collection device and, second, application of the saliva specimen to the analytical device described in those inventions.

This is disadvantageous as the risk of making errors by untrained users increases when the number of operations and reagents increases. Thus, based on the foregoing, it is clear that it is highly desirable to make available tests for saliva analysis that are simpler than those available now. More specifically, it is clear that a saliva assay device that provides for substantially contemporaneous saliva collection and assay would be highly desirable.

OBJECTS OF THE INVENTION

It is an object of the invention to solve the problems of the prior art. More specifically, it is an object of the invention to provide a device that provides for collection of saliva and detection of one or more analytes therein.

It is an even more specific object of the invention to provide a device having the following:

(a) at least a portion (a) for saliva collection comprised of an absorbent material that when placed in the mouth provides for saliva absorption and flow onto a second portion (b) with which (a) is in contact, (b) at least one portion (b) that comprises a solid support constituted of an absorbent material that provides for the immunochromatographic assay of saliva, which comprises a visual read area on which visual detection of the presence or absence of an analyte can be seen after the assay is complete, on which visual reading area is directly or indirectly bound (1) at least one ligand that specifically binds the analyte that is to be detected;

(2) at least one tracer that is comprised of the analyte labeled with a visually detectable particulate label without the need for any other visual detection device;

(3) an area within the visual read area that contains a line or other visually detectable area indicative of the presence or absence of the analyte being detected and optionally a control area that contains a line or other visually detectable area that indicates that the assay is completed;

(c) at least one area (c) that is in contact with (b) at least at one end, which is comprised of an absorbent material that provides for the flow of saliva from (b) toward the end of the device opposite the end at which saliva collection occurs;

(d) a holder that contains the area (b) and (c), and which comprises at least one cut-out portion that provides for visual detection of the visual read area contained in (b) after assay has been completed; and (e) optionally a removable cover that can be placed over the holder (d), thereby covering the portion (a) that is used for collection of saliva.

It is another specific object of the invention to use such devices for testing saliva samples for specific analytes.

It is another object of the invention to provide kits containing the subject devices designed for testing saliva for specific analyte(s).

SUMMARY OF THE INVENTION

The subject invention provides an immunoassay device that can simply collect saliva from a person's mouth and also perform immunoassays on the saliva to determine the presence and/or amount of analytes in the saliva without the need for manipulation of the saliva or use of instrumentation outside of the device, and which provides for a visual readout of the results, i.e., the presence or absence of a particular analyte. This will allow simple collection and analysis sequentially without further manipulation of the saliva sample or the device.

Such a device also desirably provides for the collection of the saliva sample and the determination of analytes in a particular saliva sample outside of the typical laboratory setting by combining the two processes, collection and testing. Thus, the subject invention will allow for field tests by law enforcement for drugs of abuse and analysis of medicines and endogenous substances in saliva to be effected by non-laboratory personnel and for assays to be performed quickly and simply, i.e., without the need to involve a laboratory technician or setting. This should afford benefits both in terms of convenience and reduced costs.

Combining the collection of specimen and the analysis into a single device with no operations or reagents necessary will greatly simplify such testing and allow untrained users to perform such collection and analysis. With no manipulation of the device or addition of reagents, untrained users simply insert the collection end of the device into the mouth of the person from whom the saliva is collected. No further operations are required and the test results are read on the device by a visual readout, such as the presence or absence of a colored line in the test read area. In addition, such simple testing of saliva will allow the testing to take place outside of the laboratory in locations such as the roadside, police stations, prisons, factories and other workplaces, the home, the hospital bedside and practically any location. Accordingly, this should eliminate the need for costly laboratory testing procedures, which should result in considerable cost savings for the subject device.

Thus, the present invention simplifies the prior process for saliva testing by combining the collection and testing operations and device into one simple to use device that simultaneously collects and tests the saliva. Also, in a preferred embodiment, the present invention will allow no contact with the saliva by the testing person. This will be accomplished by a removable cover that will optionally cover the end of the device which provides for saliva collection.

More specifically, and in accordance with one aspect of the present invention, there is provided a simple and direct means to collect saliva from a person's mouth into a drug assay device by means of one or more absorbent materials that extend out from one end of the device, which absorbent materials are placed in contact with saliva in the mouth. The saliva is collected because of the absorption and capillary flow of the saliva through the absorbent material into the device. Moreover, in the subject immunoassay device, such absorbent material or materials will preferably be directly attached to the solid support upon which the immunodetection reactivity for one or more analytes is effected. In this way, the simple collection of the saliva sample and initiation of the immunoassay for the analytes can be performed substantially contemporaneously, i.e., as soon as enough saliva has been absorbed to initiate contact with the solid support on which one or more immunoreactions is effected.

In accordance with a preferred aspect of the present invention, a cover, typically a plastic cover, is part of the device. The purpose of this cover is to protect the absorbent material that projects from one end of the device for the saliva collection. This plastic cover is removed prior to insertion of the absorbent material end of the device into the person's mouth. After saliva collection is complete, this plastic cover is replaced over the absorbent material end of the device to shield the absorbent material that contains saliva. Thus, this obviates the problem of potential contact by the testing person with the saliva in the absorbent material after the cover is placed on the device. This is significant, particularly in the context of detection of illegal drugs, when it is important that the results should be accurate and not subject to error because of potential contamination by an unskilled user, e.g., a law enforcement official.

In accordance with another preferred aspect of the present invention, there is provided a means for the assay of various analytes by the method of immunoassay on a solid support with visual readout for saliva specimens. The subject invention allows for the detection of analytes even in low concentrations, e.g., as low as about 1 ng/ml to 500 ng/ml, in saliva by a simple visual read of the result area(s) on the solid support. Visual readout is obtained by use of tracers that contain a colored label such as colored latex particles, colloidal metals or liposomes containing a dye. The use of reagent impregnated test-strips in specific binding assays has been previously reported, see, for example, in EP-A 0225054 (WO-A 8702774), U.S. Pat. No. 4,624,929, EP-A 02174406 and EP-A 0291194. This invention allows simple collection and testing of saliva for specific analytes in a single device.

As noted previously, the present invention provides an immunoassay device that provides for both saliva collection and analysis which requires no operation or reagent additions other than the simple collection of saliva via absorption by the device from the mouth. Thus, the device allows collection and testing of saliva for various analytes by unskilled users in remote locations. Accordingly, the device of the subject invention is characterized by the following advantages over previously described assays and methods:

a) it does not require a separate device and method for collection of the saliva specimen:
b) it does not require pipetting or other specimen manipulation;
c) it does not require exact volume measurement of specimen;
d) it does not require a separate device and method for analysis of the saliva specimen;
e) it only requires a single step, i.e., insertion of the device into the mouth, to perform both saliva specimen collection and initiation of the analysis for various analytes;
f) it does not require time measurements;
g) it provides for rapid results, i.e., it enables saliva collection and test results in less than ten minutes;
h) it provides for detection of even low concentrations of analyte (detection limit, approximately about 5 nanograms per milliliter);
i) it does not require introduction of any additional liquid reagents, thereby avoiding any possible confusion by non-laboratory users;
j) it optionally provides for containment of the saliva exposed portion of the device by replacement of an optimal protective cover over the absorbent area used for saliva collection, thereby reducing risk of potential environmental contamination;
k) it optionally comprises a built-in test validation by the visual readout of a colored line or area indicating test completion and proper performance; and
l) it provides for highly accurate visual reading of results based on the presence or absence of a colored line or area for each analyte;

To the best knowledge of the inventor, no assay method or device previously described exhibits all of these properties combined in the same collection and analytical system detection of analytes in saliva. The above mentioned advantages are inherent to the device and the method of the invention, based on the principles of direct saliva collection by an absorbent material that allows flow, preferably by capillary action, of saliva onto the solid support for immunoassay for analysis of various analytes in the saliva with simple visual readout of test results.

In general, the device according to the invention will comprise of the following parts:
a) a first portion, consisting of a material that is highly absorbent and able to draw saliva by capillarity, and allows lateral flow of analyte components in the saliva, that extends out from one end of the device and is designed to be placed inside an individual's mouth for contact with saliva and absorption of saliva, while the other end extends into the device and contacts with the following b) portion;
b) a second portion comprising a solid support, such as nitrocellulose, that allows the immunochromatographic assay of the saliva by capillary flow and includes a visual reading area, on which is bound:
  1) a protein or proteins that are able to selectively bind an analyte and
  2) a tracer or tracers that are comprised of a ligand (the analyte) labeled with a colored particulate label and
  3) at least one area on the solid support within the visual read area which provides a visually detectable line or area after analytes based on the presence or absence of a specific analyte, and optionally a control area or line which is detectable when the saliva has flowed through the entire visual read area and the assay is thus complete;
c) a third portion, at least one portion of which contacts the previous one, comprised of a material that facilitates the capillary flow of the saliva towards the end of the device opposite from the end that saliva collection is effected;
d) a holder, typically of plastic (and which holder also typically contains at least one cut-out portion), that contains b), and c); and
e) optionally, a removable cover, typically made of plastic, that fits onto d) and covers a), the collection end of the device, thereby obviating the risk for contamination of saliva after collection.

Moreover, in order to assay for multiple analytes, the device may have one or more saliva collection and assay components consisting of the three portions described above in a), b), and c). Thus, based on the foregoing, the subject device provides for high sensitivity by the use of a visible tracer, without instrumentation, which is visually detected on the solid support b) under assay conditions and without further treatment thereof.

DETAILED DESCRIPTION OF THE FIGURES

FIG. 1 shows one embodiment of the invention seen in top view, wherein the subject saliva immunodetection device comprises a single saliva collection and assay component area "B". In the Figure, "A" depicts an optionally removable cover, typically made out of a plastic material, that optionally covers the saliva collection end and assay component portion of the device B. In the Figure, "C" refers to the end of a holder "D", typically comprised of a plastic material, which holder keeps the saliva collection and assay component(s) B, in place and provides a means to hold the device while inserting into the mouth for saliva collection. The plastic cover D, as depicted in the Figure, has a cutout portion "E" that allows viewing of the portion of the saliva collection and assay component(s) B, on which the immunochromatographic assay(s) take place and the visual readout is accomplished.

Figure 2:
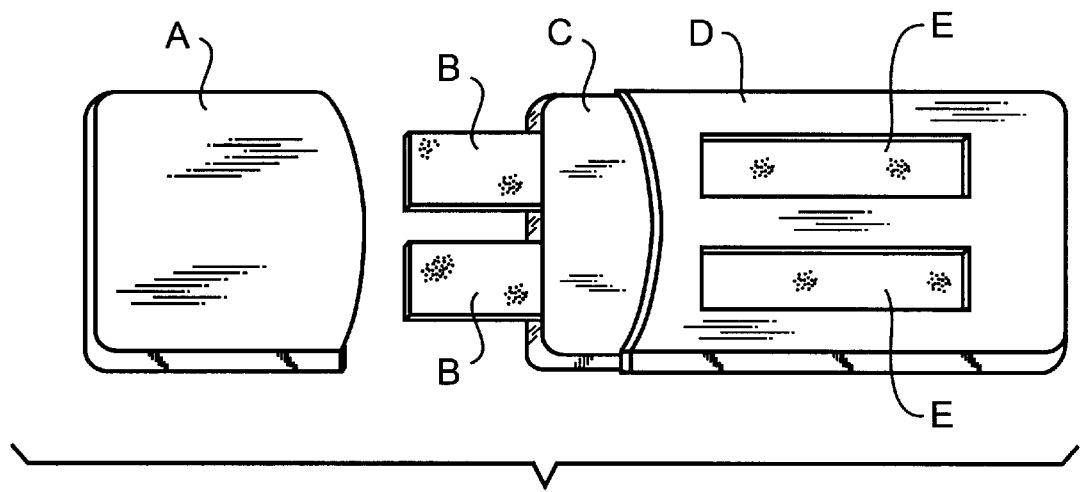

FIG. 2 depicts another embodiment of the invention. The device, also shown in top view, is the same as that in FIG. 1 except that there are two saliva collection and assay component areas, "B", and two cutout areas "E", in the holder D, in which visual detection results can be seen after an assay has been completed.

Figure 3:
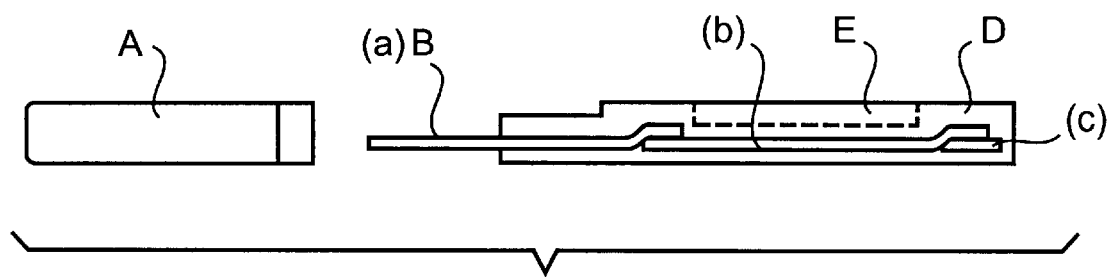

FIG. 3 shows a side view of an assay device according to the invention which comprises a single saliva collection and assay component "B". The figure illustrates that "B" actually consists of three parts, (a), (b) and (c), that are sequentially contacted with saliva; (a) consisting of a highly absorbent material that extends from one end of the device and which is placed inside a subject's mouth, thereby providing for saliva absorption, the (b) area which is held inside the "D" holder that comprises a solid support that provides for immunochromatographic assay of saliva by capillary flow and includes a visual reading area, and (c) a portion in contact with (b) that comprises a material that provides for capillary flow of saliva from the end of the device from which saliva is collected toward the other end of the device.

Thus, in the above mentioned Figures, the reference letter "A" shows the cover for the device, the reference letter "B" shows the saliva collection and assay component(s), the reference letter "C" shows the end of the plastic holder over which the plastic cover "A" fits snugly, the reference letter "D" shows the holder for the device, and the reference letter "E" shows the cutout(s) in the holder "D" through which the test read area of "B" can be seen. In FIG. 3, the reference letter "(a)"shows the first portion of "B" that extends out of the device and is designed to be placed inside the mouth for the absorption and capillary flow of saliva into the device, the reference letter "(b)" shows the solid support portion of "B" that contains the reagents (binders, tracers and any others) for the immunochromatographic assay(s) and the test read areas, and the reference letter "(c)" shows the further area that contacts "(b)" and consists of a material able to assure the complete capillary flow of saliva though "B".

DETAILED DESCRIPTION OF THE INVENTION

Thus, as can be seen from the figures, the subject immunoassay device may comprise one or more saliva collection and assay component(s), (B), which themselves comprise three discrete areas, (a) a highly absorbent area providing for saliva collection that is placed in contact with a subject's mouth, (b) a solid support in contact with (a) that provides for immunochromatographic assay of saliva by capillary flow, and (c) an area in contact with (b) that comprises a material that facilitates the flow of saliva to the end, or nearly the end, of the device opposite to the end that saliva collection was effected.

The materials of "(a)" and "(b)" allow lateral flow of saliva and analytes within the saliva.

Moreover, as can further be seen from the figures, the "a" portion of "B" will preferably be protected from contamination by in a removable cover which is placed thereon after saliva collection, with the "(b")" and "(c)" portions being contained within "D", a holder, which has at least one cutout portion "E" that permits visual detection of results of the immunochromatographic assay that is effected in (b), with the results being seen in the visual detection area as a detectable line or other visually detectable area.

More specifically, the "(a)" portion will preferably be comprised of any absorbent material that is able to be safely placed within a subject's mouth, that provides for sufficient absorption of saliva for the saliva to flow onto the "(b)" portion, the solid support on which the immunochromatographic assay is conducted. By sufficient is meant that saliva will be sufficiently absorbed after being placed for a sufficient time in a user's mouth, e.g., about 10 to 120 seconds, with sufficient saliva typically being at least about 0.2 to 4 ml.

Suitable absorbent materials include by way of example nitrocellulose, cellulose acetate, polyethersulfur fabric, paper, fiberglass, polycarbonate, polypropylene, acetate, chemically modified paper, and combinations thereof, e.g., glass fiber containing cellulose material, or other materials providing good lateral flow rates of saliva. The absorbent materials allow lateral flow of potential analytes contained in the saliva.

Typically, the "a" portion that is placed inside the subject's mouth and which provides for saliva collection will range in length from about 0.5 to 4 cm, have a width of about 0.8 cm to 4 cm, and a thickness ranging from about 0.1 to 0.4 cm. However, these dimensions may vary widely largely dependent upon the particular user's mouth and specifically the varying mouth size of different users, e.g., children versus adults. The material of "a" may further comprise a support material such as Mylar attached to improve strength.

As noted above, the "(a)" portion of "B" will optionally be covered by a detachable cover, typically comprised of a plastic material, that preferably will fit snugly over the device, and will prevent "(b)" from being contaminated after saliva collection has been effected. This cover is not mandatory as other precautions can be taken to prevent contamination of saliva and the saliva collection portion of the device afier use. This cover "A", if present, will typically range in length from about 1 to 7 cm, width of 1.5 to 9 cm, and thickness of about 0.2 to 2 cm, and will be designed such that it fits snugly over the device, specifically covering up to the "C" portion of the device and shown in FIGS. 1 and 2. The "A" cover can alternatively be comprised of other materials such as cardboard, or metals such as aluminum.

The "(b)" portion of the device is where the immunochromatographic reaction takes place that provides for detection of one or more analytes, and on which visual readout is accomplished. This area will comprise a solid support, comprised of an absorbent material that allows for immunochromatographic assay of saliva by capillary flow that includes a visual reading area on which is directly or indirectly bound one or more of the following;

1) a binding partner, typically a protein such as an antibody that specifically binds an analyte;
2) a "tracer" that is comprised of a ligand (the analyte) labeled with a colored particulate label; and
3) a "visual read area" or "test read area" that comprises at least a first area on the solid support portion "(b)" that provides a visually detectable line or other visible area, e.g., circle, triangle, square, etc., when the assay is complete that provides an indication of the presence or absence of analyte; and optionally a second area, also on the solid support within the visual read area that results in a visually detectable control line or other detectable portion when the assay is completed for the respective analyte.

As can be seen from the Figures, the "(b)" area is held inside the holder "D". The "(b)" area will preferably comprise a solid support strip, comprised of an absorbent material, e.g., selected from the above-identified materials, contained within a casing "D" that typically ranges in length from about 2 to 25 cm, width of about 1.5 to 8 cm, and a thickness of about 0.2 to 1.5 cm.

These materials include, in particular, nitrocellulose, fabric, nylon, cellulose acetate, or any other material on which the desired immunochromatographic assay can be effected. This requires that the material allow saliva and analyte in the saliva to flow through it and also support the requisite reagents, binders, tracers, and any other materials necessary for immunoassay.

More specifically, the solid material that comprises "(b)" will be a material that has a surface area (area/weight of material) that allows for the binder to be supported in a concentration (weight/unit area) such that the tracer is visible under assay conditions. The term "visible" means that the label on the tracer can be seen without the need for extraneous instruments, i.e., by use of the naked eye. The visibility of the tracer in visual read area of "(b)" allows for the determination of the presence or absence of the tracer, and/or the intensity of the visible tracer. This, in turn, allows for the determination of the presence or absence of analyte, based on the presence or absence of such visually detectable signal, e.g., colored line. Also, the intensity of the visually detectable signal provides a semi-quantitative means of determining the relative amount of the analyte being detected in the saliva sample, e.g., an illegal drug, therapeutic drug, endogenous biomolecule, alcohol, biometabolite, etc.

As noted previously, at least one portion of the strip "(b)" will be exposed by a cutout "E", in the plastic holder "D", which includes the read area of "(b)". The material of "(b)" can be nitrocellulose, fabric, nylon, cellulose acetate or any other material on which the assay can be effected. Moreover, the material will also allow the saliva and analytes in the saliva, to flow through it while supporting the reagents, binders, tracers and any others, for the immunoassay for the analyte(s).

The binder(s) which is supported on the solid support strip "(b)" is either a binder for both the analyte(s) and tracer(s), or a binder(s) for only one of the analyte and tracer, with the type of binder(s) which is used being dependent upon the type of assay which is being utilized for determining the analyte(s). For example, if the assay(s) is a competition type of assay, then the binder(s) supported on "(b)" would be a binder(s) for both the tracer(s) and analyte(s), whereby both tracer and analyte would compete for a limited number of binding sites on the binder.

If the assay is a so-called "sandwich" type of assay, then the binder(s) which is supported on the solid support "(b)" is a binder(s) for only the analyte(s). In such an assay, the tracer(s) is a tracer which is specific for the analyte, whereby tracer is bound to the analyte which is bound to the supported binder.

If the assay is an inhibition type assay, then the supported binder(s) is specific for only the tracer(s), and the tracer is also specific for the analyte. In such an assay, the presence of analyte inhibits binding of tracer to the supported binder. Thus, the tracer when bound to the solid support "(b)" is either directly bound to the binder on the support or is bound to analyte which is bound to binder on the solid support "(b)".

The type of binder(s), which is(are) used in the subject assay, is(are) dependent upon the analyte(s) to be assayed, as well as the specific assay procedure. As known in the art, the binder(s) which is(are) supported may be an antibody including monoclonal antibodies, a binding fragment thereof, an antigen, a protein specific for the material to be bound or a naturally occurring binder.

The binder(s) is supported on the solid support "(b)" in the test read area by applying a solution of the binder(s) to a defined area of the solid support, such as, for example in the form of a line, circle or other area. The concentration of the binder(s) placed in the defined area of the solid support "(b)" will vary depending upon the assay(s) to be performed; however, the binder(s) is(are) generally present in a concentration of at least 1 microgram/square centimeter and, preferably at least 40 microgram/square centimeter. The test read area may contain more than one test area, either with the same binder being applied to each test read area, optionally with different affinities and/or in different concentrations, or the various test areas may include different binders, in which case, the device may be used for determining more than one analyte on a solid support strip "(b)". The device may contain more than one solid support strips "(b)" for additional analytes or determining one analyte in various concentrations. Although the binder(s) may be appropriately applied to the test area(s) of the solid support strips "(b)" for support thereon by adsorption, it is also to be understood that in some cases it may be necessary or desirable to provide for covalent coupling of the binder to the solid support "(b)".

The ligand(s) which is labeled for use as the tracer(s) in the assay(s) of the present invention is also dependent upon the analyte(s) to be assayed, as well as the assay procedure. For example, if a competitive assay is being used for determining antigen or hapten, the ligand used in producing the tracer(s) would be either the analyte(s) or an appropriate analog thereof. If the assay is a "sandwich" type of assay for an antibody, then the ligand(s) used in producing the tracer (s) would be a ligand which is specific for the analyte to be assayed.

In producing the tracer(s) the ligand(s) is labeled with a particulate label, which is visible, whereby the tracer(s), when used in the assay, is visible. This type of label may include stained bacteria, colored latex particles, hydrophobic dyes, colloidal metals able to bind proteins when adjusted to the optimal pH and concentration (gold, silver, platinum, copper, and the metal compounds sodium hydroxide, silver iodide, silver bromide, copper hydroxide, aluminum hydroxide, chromium hydroxide, vanadium oxide, arsenic iodide, manganese hydroxide and the like). Methods for coupling colored particles to proteins are well known to those skilled in the art and are described in the afore-cited references.

As explained previously, the material of "(b)" allows the saliva to flow through it while supporting the reagents (binders, tracers and any others) for the immunoassay for the analyte(s). Thus, the solid support "(b)" for the reagents has capillary properties and is able to assure the elution of the colored bioselective reagents thanks to the action of the capillary forces at the saliva passage. The test read area of "(b)" optionally includes a test area that will visually indicate when the test has finished. Such an area is called a "Test Valid" area and includes an area on the solid support "(b)" where a binder is supported that will bind tracer to the extent that a visual area, such as a line or circle, will be produced when the device has completed the analysis for analytes. Therefore, there will be within the test read area of the solid support strip "(b)"(preferably) one or more areas that will show visual read areas for the analyte(s) and optionally one or more for the Test Valid visual read.

As also noted previously, the "(b)" area will be in contact with a "(c)" area, at least at one end. This "(c)" portion is comprised of material that allows for substantially all of the collected saliva to flow towards the end of the device opposite the end that saliva is collected. Therefore, the material that comprises "(c)" will desirably be one that allows the capillary flow of saliva towards the end of the device opposite from the collection end. Typically, such materials will be highly absorbent, with examples thereof including fabric, paper, cellulose, and other absorbent materials previously identified that will absorb the saliva as it flows through "(b)" by capillary action into the attached "(c)" material. The material of "(c)" should desirably absorb a relatively large amount of liquid relative to its weight.

Therefore, based on the design of the subject device, the only required operating steps for using such device to effect an assay is removal of the cover "A" (if present), insertion of the collection end of the device into the mouth, removal of the device from the mouth, replacement of the cover "A" (if present), and visual readout of the results of the device, preferably after the Test Valid areas show that the assay(s) is complete. In general, the assay will be complete anywhere from about 1 minute to 60 minutes after saliva collection.

Accordingly, the subject device provides for the collection and assay of saliva specimens in a single step with no manipulation of the specimen nor instrumentation for reading of the assay results. Moreover, the device preferably will have a cover that functions to shield the saliva collection portion of the device both before and after saliva collection.

Compounds which can be analyzed according to the subject invention include, by way of example, drugs of abuse such as heroin, cocaine, marijuana, etc., nicotine and metabolites, human endogenous substances such as hormones, and therapeutic drugs. Other specific examples include, by way of example, tetrahydrocannabinol, cocaine, morphine, benzoylecgonine, heroin, acetylmorphine, amphetamine, methamphetamine, phencyclidine, diazepam, alprazolam, triazolam, 11-nor-delta-9tetrahydrocannabinol-carboxylic acid, LDS, oxazepam, other benzodiazepines, butalbital, pentobarbital, secobarbital, amobarbital, butabarbital, phenobarbital, methadone, propoxyphene, methadone metabolite, nicotine, cotinine, phenytoin, theophylline, antidepressants, digoxin, antipsychotics, antibiotics, tumor markers, steroids, ethanol, methanol, anabolic steroids, anti-tumor chemotherapeutics, anti-epileptics, environmental toxins, industrial pollutants, industrial chemicals, anti-arrhythmic medications, antihypertensive medications, metals, methylenedioxyamphetamine, methylenedioxymethamphetamine, sedatives, tranquilizers, central nervous system depressants, and narcotics.

The invention also refers to a method for the simultaneous collection and assay of saliva for the determination of one or more analytes in the saliva. The method and the device of the invention allow the collection and analysis for analytes with one direct collection of saliva from the mouth and subsequent direct and clear reading of the results visually. The method and the device preferably allow collection and determination of analytes in saliva in ten minutes or less and with high sensitivity. The device can be part of a kit that includes instructions for the use of the device and method. The following Example illustrates the present invention in a non-limitative way.

EXAMPLE

A piece with dimensions of one centimeter by four centimeters was cut out of a ONitroPB nitrocellulose membrane with 8.0 micron pore size (Micron Separations Inc.). A piece with dimensions of one centimeter by 4.5 centimeters was also cut out of a MagnaGraph Nylon membrane with 5.0 micron pore size (Micron Separations Inc.). This membrane has added to it specific binders for analyte(s) of interest, in particular cocaine and tetrahydrocannabinol, in separate lines that will be in a Test Read area and a binder to trap excess antigen in a line in the Test Valid area. Tracers of colloidal gold conjugates of cocaine and tetrahydrocannabinol were added at the end of the membrane that will contact the NitroPB wick at the collection end of the plastic holder. A piece of highly absorbent paper measuring one centimeter by one centimeter was cut. The plastic holder and plastic cover are manufactured by means of injection molding from polystyrene which contains recesses for the contour of the NitroPB, the MagnaGraph Nylon and the absorbent paper. The plastic holder consists of two pieces, a bottom piece and a top piece. The NitroPB membrane, the MagnaGraph Nylon membrane and the absorbent paper are aligned in the bottom of the plastic holder in the recess contour. The NitroPB membrane extends 1.6 centimeters outside of the collection end of the plastic holder, the MagnaGraph Nylon was placed 0.5 centimeters under the other end of the NitroPB membrane inside the plastic holder bottom. The end of the MagnaGraph Nylon membrane placed under the NitroPB membrane contains the colloidal gold tracers for cocaine and tetrahydrocannabinol. Buffers and other reagents for stability were placed on the MagnaGraph Nylon membrane with the tracers. The absorbent paper was placed under the opposite end of the MagnaGraph Nylon membrane at the end of the bottom part of the plastic holder opposite of the collection end. The top of the plastic holder was placed on the bottom and snapped into place to firmly hold the membranes and paper in the proper place. The plastic cover is placed over the collection end of the assembled plastic holder. The dimensions of the entire device are 9.5 centimeters long, 2.5 centimeters wide and 0.8 centimeters thick. The entire device is sealed in an airtight foil pouch that contains a desiccant. The foil packaged device and instructions are packaged in a box.

In order to carry out a test for cocaine and tetrahydrocannabinol in a saliva specimen, the device was removed from its foil pouch and the plastic cover removed. The collection end of the device with the NitroPB membrane extending out was placed into an individual's mouth for sixty seconds. The device was removed from the mouth and the plastic cover replaced on the collection end of the plastic holder. The device was allowed to complete the assay for approximately three to eight minutes, when the Test Valid area of the Test Read window showed a visible red line. Adjacent to the Test Read area of the MagnaGraph Nylon membrane on the plastic holder was marked THC and COC. The presence of a red line next to the THC marking indicates the saliva does not contain a detectable concentration of tetrahydrocannabinol. By contrast, the absence of this red line indicated that the saliva specimen did contain a detectable concentration of tetrahydrocannabinol. The presence of a red line next to the COC marking indicates the saliva does not contain a detectable concentration of cocaine. By contrast, the absence of this red line indicates that the saliva specimen does contain a detectable concentration of cocaine.

Thus, based on the foregoing, it can be seen that the present invention can be used for the detection and/or semi-quantitative measurement of amounts of analytes in a saliva sample.

What is claimed is:

1. A method for detecting at least one analyte in the saliva of a subject suspected of containing said analyte using a device that provides for both the collection of saliva and the detection of at least one analyte contained therein, comprising the following steps:
   (i) collecting saliva in a device that provides for the simultaneous collection of saliva and detection of an analyte in said saliva wherein said device comprises the following:
      (a) at least a portion (a) for saliva collection comprised of an absorbent material that when placed in the mouth provides for saliva absorption and flow onto a second portion (b) with which (a) is in contact,
      (b) at least one portion (b) that comprises a solid support constituted of an absorbent material that provides for the immunochromatographic assay of saliva, which comprises a visual read area on which visual detection of the presence or absence of an analyte can be seen after the assay is complete, on which visual reading area is directly or indirectly bound,
         (1) at least one ligand that specifically binds the analyte that is to be detected;
         (2) at least one tracer that is comprised of the analyte labeled with a visually detectable particulate label without the need for any other visual detection device;
         (3) an area within the visual read area that contains a line or other visually detectable area indicative of the presence or absence of the analyte being detected and optionally a control area that contains a line or other visually detectable area that indicates that the assay is completed;

(c) at least one area (c) that is in contact with (b) at least at one end, which is comprised of an absorbent material tat provides for the flow of saliva from (b) toward the end of the device opposite the end at which saliva collection occurs and;

(d) a holder that contains the area (b) and (c), and which comprises at least one cut-out portion that provides for visual detection of the visual read area contained in (b) after assay has been completed; and wherein said collection of saliva is effected by placing the saliva collection end of said device in the mouth of said subject for about 10 to 120 seconds resulting in a sufficient amount of saliva being absorbed by said device to enable analyte detection;

(ii) removal of said device from the mouth; and (iii) visually detecting about one to sixty minutes after saliva collection whether said at least one analyte is present or absent by visually analyzing the visual read area on said solid support area (b) of said device.

2. The method of claim 1, wherein said visual readout of results is effected about one to ten minutes after saliva collection.

3. The method of claim 1, which is used to detect more than one analyte in a saliva samnple.

4. The method of claim 1, which is used to detect an analyte selected from the group consisting of an illegal drug, a hormone, and a therapeutic drug.

5. The method of claim 1, which is used to detect an analyte selected from the group consisting of tetrahydrocannabinol, cocaine, morphine, benzoylecgonine, heroin, acetylmorphine, amphetamine, methamphetamine, phencyclidine, diazepam, alprazolam, triazolam, 11-nor-delta-9-tetrahydrocannabinol-carboxylic acid, oxazepam, other benzodiazepines, butalbital, pentobarbital, secobarbital, amobarbital, butabarbital, phenobarbital, methadone, propoxyphene, methadone metabolite, nicotine, cotinine, phenytoir, theophylline, antidepressants, digoxin, antipsychotics, antibiotics, tumor markers, steroids, ethanol, methanol, anabolic steroids, anti-tumor chemotherapeutics, anti-epileptics, environmental toxins, industrial pollutants, industrial chemicals, anti-arrhythmic medications, anti-hypertensive medications, metals, methylenedioxyamphetamine, methylenedioxymethamphetamine, sedatives,tranquilizers, central nervous system depressants, and narcotics.

6. The method of claim 1, which is used to detect an analyte selected from the group consisting of heroin, cocaine, marijuana, and nicotine.

7. The method of claim 1 wherein said device comprises a removable cover that can be placed over the holder (d), thereby covering the portion (a) that is used for collection of saliva.

* * * * *